United States Patent [19]

Schaar

[11] 4,074,716
[45] Feb. 21, 1978

[54] DIAPER WITH ELASTIC FASTENER TAB

[75] Inventor: Charles H. Schaar, Lake Zurich, Ill.

[73] Assignee: Colgate-Palmolive Company, New York, N.Y.

[21] Appl. No.: 756,309

[22] Filed: Jan. 3, 1977

[51] Int. Cl.² .............................................. G61F 13/16
[52] U.S. Cl. .................................... 128/287; 128/248; 24/73 VA
[58] Field of Search .................. 128/284, 287, 290 R; 24/DIG. 11, 73 VA

[56] References Cited

U.S. PATENT DOCUMENTS

| | | | |
|---|---|---|---|
| 3,530,859 | 9/1970 | Heimowitz | 128/284 |
| 3,771,524 | 11/1973 | Ralph | 128/287 |
| 3,800,796 | 4/1974 | Jacobs | 128/284 |
| 3,920,016 | 11/1975 | Mesek et al. | 128/287 |
| 3,920,018 | 11/1975 | Schaar | 128/287 |
| 3,995,638 | 12/1976 | Schaar | 128/287 |
| 4,036,233 | 7/1977 | Kozak | 128/287 |

Primary Examiner—Aldrich F. Medbery
Attorney, Agent, or Firm—Powell L. Sprunger

[57] ABSTRACT

A disposable diaper comprising, an absorbent pad assembly having opposed surfaces, a pair of side edges, and a pair of end edges connecting the side edges. The diaper has a tape fastener comprising, tape means having a first portion secured to one of the surfaces of the pad assembly, a securement portion for attachment to a spaced portion of the diaper, an extensible portion connecting the first and securement portions, and elastic means constraining expansion of the extensible portion.

22 Claims, 17 Drawing Figures

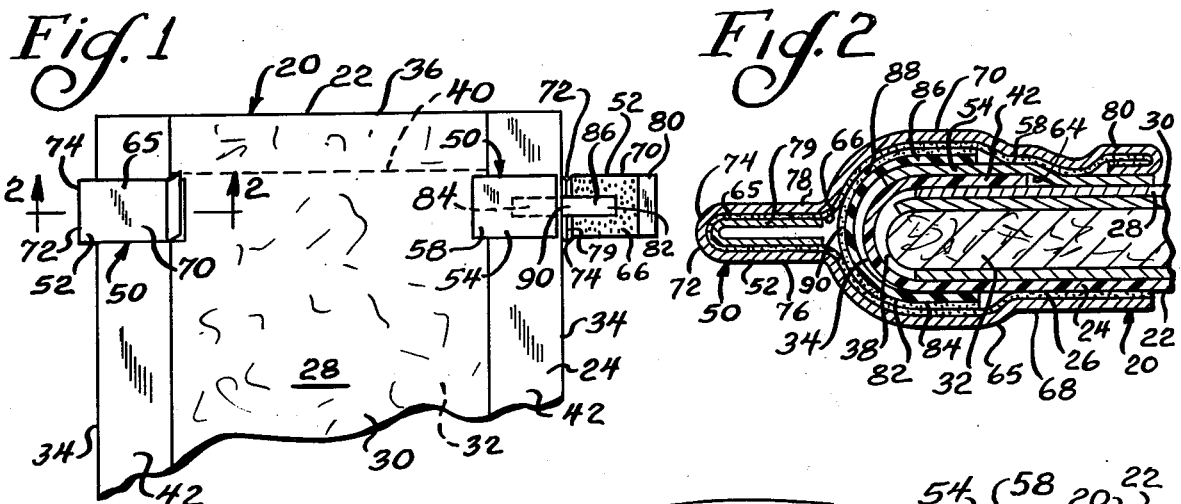
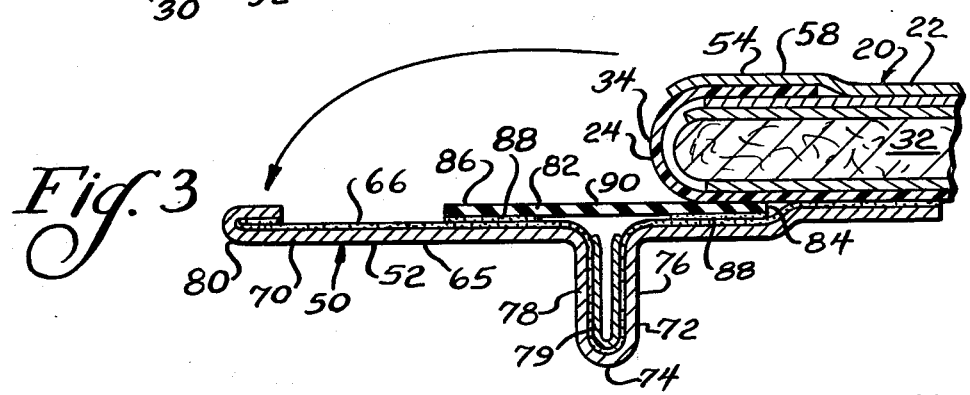
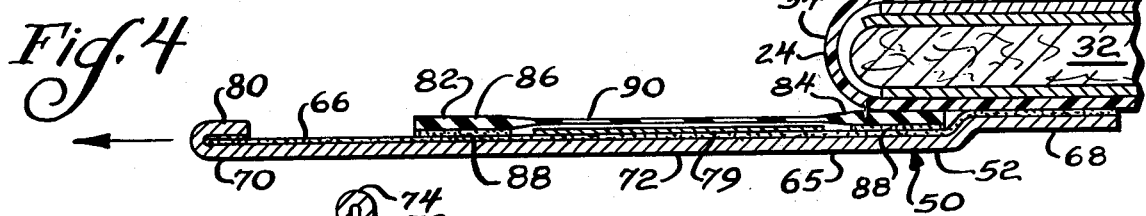
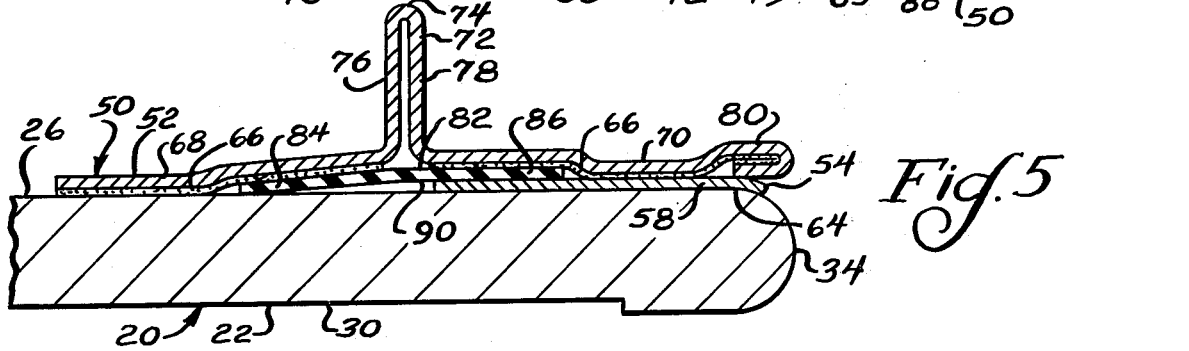
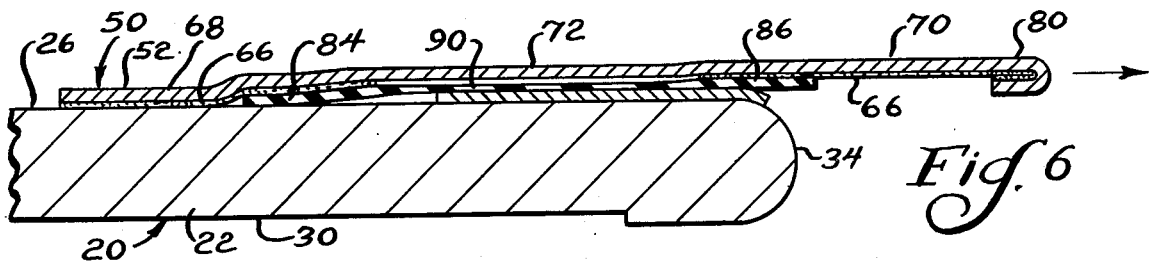

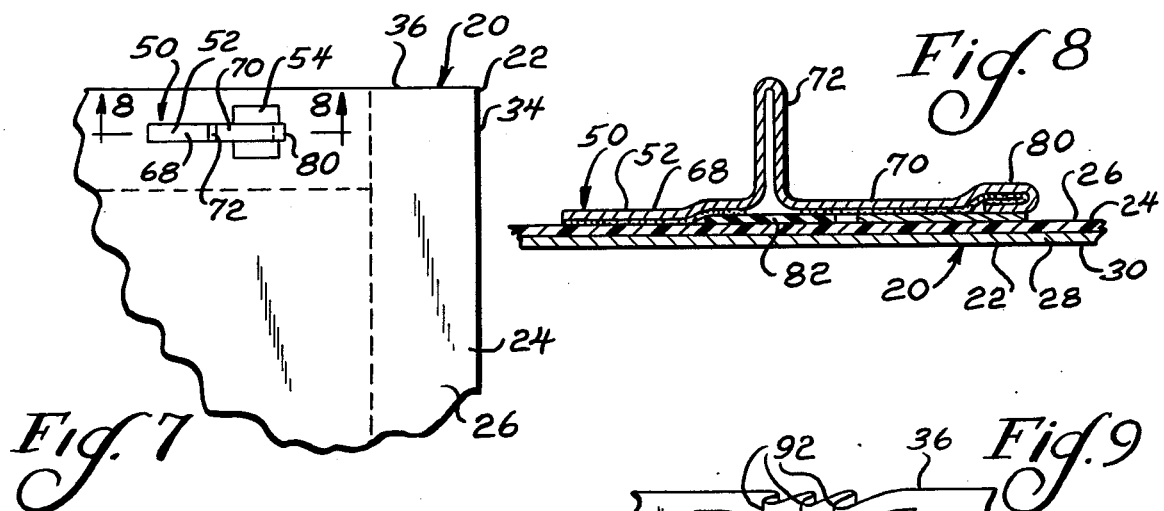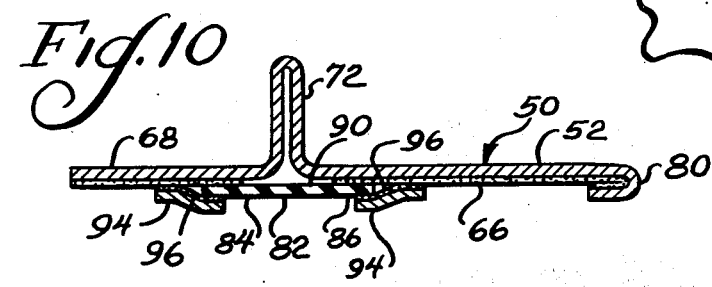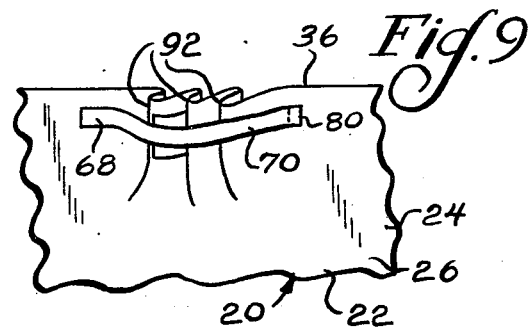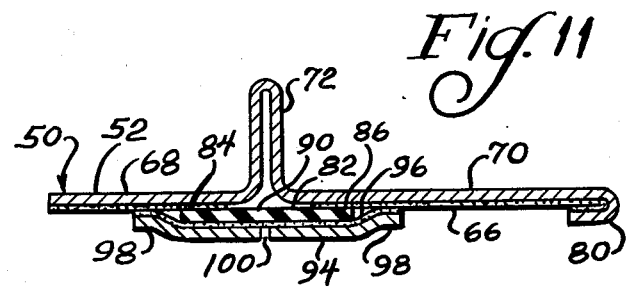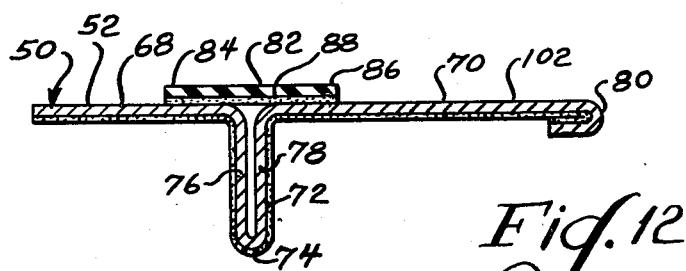

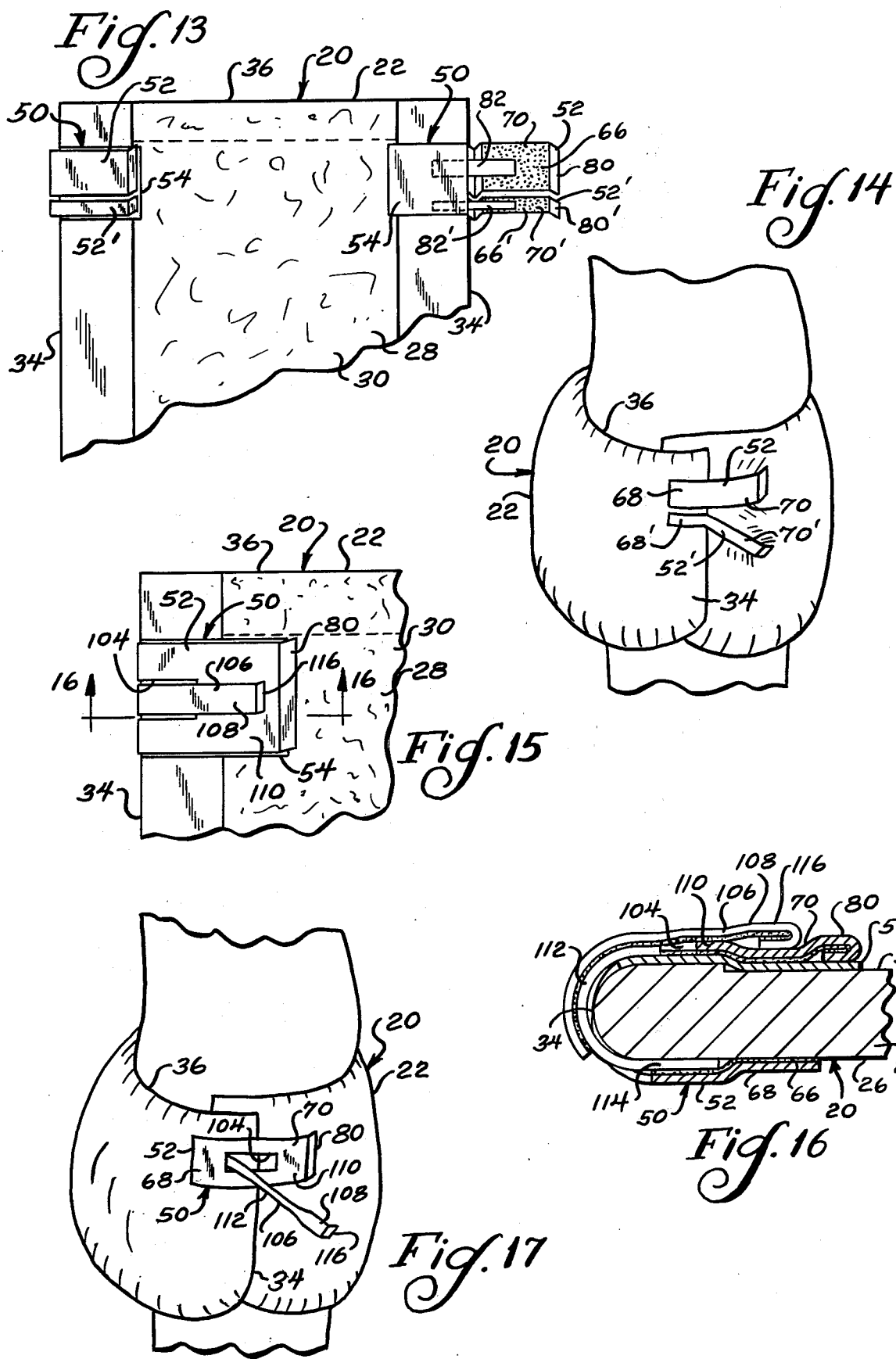

DIAPER WITH ELASTIC FASTENER TAB

BACKGROUND OF THE INVENTION

The present invention relates to absorbent articles, and more particularly to disposable diapers.

A various assortment of disposable diapers have been proposed for use on infants, and have become increasingly popular with parents since they may be discarded after a single use and need not be laundered. Such diapers are normally constructed having a fluid impervious backing sheet, a fluid pervious top or cover sheet, and an absorbent pad intermediate the backing and cover sheets.

Many of the diapers have been provided with tape fasteners which are used to secure the diaper about the infant. Such fasteners generally take the form of a pressure-sensitive tape strip having a first end attached to the diaper and a second securement end which is attached to the diaper during placement. Prior to use, adhesive on the securement end is covered to prevent premature contact of the adhesive against the diaper or other article.

An overriding consideration in construction of the diaper is the cost of manufacture and the diaper materials, since the diaper must be inexpensive to the consumer due to its disposability. Accordingly, the backing sheets of such diapers have been made from a relatively thin plastic material, such as polyethylene, in order to reduce the cost of the backing sheet and the diaper. However, it has been found that when forces are applied to the tape strip during placement and use of the diaper, the tape strips have a tendency to tear the backing sheet and become ruptured from the diaper, thus rendering the diaper relatively useless. Additionally, it is desired that the tape fastener provides a snug fit and prevents a loose fit of the diaper about the infant.

SUMMARY OF THE INVENTION

A principal feature of the present invention is the provision of a disposable diaper having an improved tape fastener.

The diaper of the present invention comprises an absorbent pad assembly having opposed surfaces, a pair of side edges, and a pair of end edges connecting the side edges. The diaper has a tape fastener comprising, tape means having a first portion secured to one of the surfaces of the pad assembly, a securement portion for attachment to a spaced portion of the diaper, an extensible portion connecting the first and securement portions, and elastic means constraining expansion of the extensible portion.

A feature of the present invention is that the extensible portion permits enlargement of the tape means responsive to forces applied to the tape strip, thus permitting conformability of the diaper about the infant during use.

Another feature of the invention is that the extensible portion reduces the forces applied to a backing sheet in shear during placement and use of the diaper, and minimizes the possibility that the tape means may rupture from the diaper backing sheet.

Still another feature of the invention is that the elastic means constrains the extensible portion to provide a snug fit of the diaper about the infant while permitting expansion of the extensible portion.

Yet another feature of the invention is that the extensible portion limits the amount of expansion of the tape means and prevents a loose fitment of the diaper which otherwise might be caused by a completely elastic tape strip.

Further features will become more fully apparent in the following description of the embodiments of this invention and from the appended claims.

DESCRIPTION OF THE DRAWINGS

In the drawings:

FIG. 1 is a fragmentary front plan view of a disposable diaper having a tape fastener of the present invention;

FIG. 2 is a fragmentary sectional view taken substantially as indicated along the line 2—2 of FIG. 1;

FIG. 3 is a fragmentary sectional view of the diaper of FIG. 2 showing the tape fastener in an unfolded configuration preparatory to use;

FIG. 4 is a fragmentary sectional view of the diaper of FIG. 3 showing the tape fastener in an extended configuration;

FIG. 5 is a fragmentary sectional view of the diaper showing another embodiment of the tape fastener of the present invention;

FIG. 6 is a fragmentary sectional view of the diaper of FIG. 5 showing the tape fastener in an extended configuration;

FIG. 7 is a fragmentary back plan view of a diaper showing another embodiment of a tape fastener of the present invention;

FIG. 8 is a fragmentary sectional view taken substantially as indicated along the line 8—8 of FIG. 7;

FIG. 9 is a fragmentary back plan view showing the fastener of FIG. 7 in an extended configuration during use;

FIG. 10 is a sectional view of another embodiment of the fastener of the present invention;

FIG. 11 is a sectional view of another embodiment of the fastener of the present invention;

FIG. 12 is a sectional view of another embodiment of the fastener of the present invention;

FIG. 13 is a fragmentary front plan view of a diaper having another embodiment of the fastener of the present invention;

FIG. 14 is an elevational view showing the fastener of FIG. 13 in an extended configuration during use;

FIG. 15 is a fragmentary front plan view of a diaper showing another embodiment of the fastener of the present invention;

FIG. 16 is a sectional view taken substantially as indicated along the line 16—16 of FIG. 15; and FIG. 17 is an elevational view showing the fastener of FIG. 15 attached to a remote portion of the diaper during use.

DESCRIPTION OF THE PREFERRED EMBODIMENTS

Referring now to FIGS. 1 and 2, there is shown a disposable diaper generally designated 20 having an absorbent pad assembly 22. The pad assembly 22 has a fluid impervious backing sheet 24, such as polyethylene, defining a back surface 26 of the pad assembly, a fluid pervious cover or top sheet 28, such as a non-woven material, defining a front surface 30 of the pad assembly 22, and an absorbent pad 32, such as comminuted wood pulp termed in the art as fluff, located intermediate the backing sheet 24 and cover sheet 28. The pad assembly 22 has a pair of side edges 34, and a pair of end edges 36 connecting the side edges 34. The absorbent pad 32 also has a pair of side edges 38 and end edges 40 connecting the side edges 38. In a preferred form, as shown, the side edges 38 of the pad 32 are located adjacent the side edges 34 of the pad assembly 22, and the fluid impervious backing sheet 24 has lateral side margins 42 folded over and secured to the top sheet 28, such that the backing sheet side margins 42 cover lateral side margins of the absorbent pad 32.

The diaper has a pair of tape fasteners generally designated 50 having a pressure-sensitive tape strip 52 and a release sheet 54, with each of the fasteners being located adjacent a side edge 34 of the pad assembly 22. The release sheets 54 have an outer release surface 58 and are attached to the front surface 30 of the pad assembly adjacent the side edges 34 by suitable means, such as adhesive 64. The release sheet 54 may be made from any suitable material, such as paper or polyethylene, and the outer release surface 58 of the paper release sheet may be formed by a suitable silicone treatment or coating.

The tape strip 52 has a relatively inextensible backing 65, such as paper, adhesive 66 on a front surface of the backing 65, a first end portion 68 secured to the back surface 26 of the pad assembly by the adhesive 66 adjacent the side edge 34, a securement end portion 70 remote the first portion 68 and having its adhesive 66 releasably attached to the outer release surface 58 of the release sheet 54, and an extensible central portion 72 extending between and connecting the first end portion 68 and securement end portion 70. As shown, the central portion 72 of the tape strip 52 has a fold about a laterally extending fold line 74 defining a first section 76 extending between the fold line 74 and first end portion 68 of the tape strip 52, and a second section 78 extending between the fold line 74 and the securement end portion 70 of the tape strip 52. The first and second sections 76 and 78 of the tape strip 52 include adhesive on their front surfaces, and the tape fastener has a sheet 79 of suitable material, such as paper, covering the adhesive on the first and second sections 76 and 78 to prevent attachment between the first and second sections during use. As shown, the securement portion 70 of the tape strip 52 may have a folded over and end defining a tab 80 to facilitate removal of the tape strip from the release sheet.

The fastener 50 also has an elastic strip 82 extending across the folded extensible portion 72 on the front surface of the tape strip 52, and having opposed ends 84 and 86 attached to the adhesive 66 on the first portion 68 and securement portion 70. The strip 82 may be made of any suitable elastic material, such as an elastic tape, product No. Y482, sold by Minnesota Mining and Manufacturing Company. As shown, the elastic strip 82 may have adhesive 88 on its ends 84 and 86 attached to the adhesive 66 and which may extend through a central part 90 of the strip 82.

With reference to FIGS. 1 and 2, the tape fastener 50 is shown in a folded configuration prior to use of the diaper, with the tape strip 52 being releasably attached to the outer release surface 58 of the release sheet 54. In use, the tab 80 may be grasped in order to peel the securement portion 70 of the tape strip 52 from the release surface 58 of the release sheet 54, as shown in FIG. 3, such that the securement portion 70 of the tape strip 52 extends beyond the side edge 34 of the pad assembly 22. With reference to FIGS. 3 and 4, when the securement portion 70 is pulled, the extensible portion 72 unfolds and longitudinally extends while the elastic strip 82 constrains longitudinal expansion of the extensible portion 72. In this manner, the extensible portion 72 permits expansion of the tape fastener during placement and use of the diaper to reduce forces otherwise applied in shear to the diaper backing sheet 24, thus minimizing the possibility that the backing sheet may be torn and tape strip may be ruptured from the diaper. At the same time, the elastic band 82 constrains expansion of the extensible portion 72, and causes a close fit of the diaper about the infant. In addition, with reference to FIG. 4, the extensible portion 72 limits the amount of longitudinal expansion of the tape strip 52 and elastic strip 82, and prevents overextension of the tape strip which otherwise might cause a loose fitment of the diaper about the infant.

Another embodiment of the tape fastener is illustrated in FIGS. 5 and 6, in which like reference numerals designate like parts. In this embodiment, the release sheet 54 is attached to the back surface 26 of the pad assembly 22 adjacent the side edge 34, and the first portion 68 of the tape strip 52 is spaced from the side edge 34 and located adjacent the release sheet 54. As before, the elastic strip 82 is connected between the first and securement portions 68 and 70, and the adhesive 66 on the securement portion 70 is releasably attached to the release surface 58 of the release sheet 54. However, if desired, the front surface of the first and second strip sections 76 and 78 may be free of adhesive to prevent attachment during use of the fastener. Also, the elastic strip 82 is attached directly to the adhesive 66 on the tape strip 52 without additional adhesive on the elastic strip or band 82.

In use, the securement portion 70 of the tape strip 52 is peeled from the release sheet 54, and the securement portion 70 is drawn past the side edge 34 of the pad assembly 22 while the first and second sections 76 and 78 unfold about the fold line 74. When the outer end of the tape strip has been fully extended past the side edge 34, as shown in FIG. 6, the securement portion 70 of the tape strip 52 is located at a position for attaching the tape strip to another portion of the diaper during placement on an infant while the elastic strip 82 longitudinally constrains the strip 52. In this manner, the tape strip 52 may be readily removed from the release sheet 54 and extended into a configuration for use in securing the diaper.

Another embodiment of the present invention is illustrated in FIGS. 7–9, in which like reference numerals designate like parts. The fastener of this embodiment is similar to the fastener discussed in connection with FIGS. 5 and 6, except that the tape strip 52 is aligned with an edge of the pad assembly 22, such as the end edge 36. Thus, with reference to FIG. 9, after the securement portion 70 has been removed from the release sheet 54, the pad assembly 22 may be gathered and the tape strip may be utilized to secure tucks 92 in the diaper between the first portion 68 and the securement portion 70 which is attached to the diaper, resulting in a snug fit of this part of the diaper about an infant.

Another embodiment of the present invention is illustrated in FIG. 10, in which like reference numerals designate like parts. In this embodiment, the fastener has a pair of relatively short anchoring strips 94 having adhesive 96 attached between the opposed ends 86 and 84 of the elastic strip 82 and the securement portion 70 and first strip portion 68 in order to enhance the attachment of the elastic strip 82 to the tape strip 52.

Another embodiment of the present invention is illustrated in FIG. 11, in which like reference numerals designate like parts. In this embodiment, the fastener 50 has an anchoring strip 94 having a length greater than the length of the elastic strip 82 and having opposed ends 98 attached by adhesive 96 to the adhesive 66 on the tape strip 52. The anchoring strip 94 has a slit 100 separating end portions of the anchoring strip 94 intermediate the ends 84 and 86 of the elastic strip 82 to permit expansion of the elastic strip 82.

Another embodiment of the present invention is illustrated in FIG. 12, in which like reference numerals designate like parts. In this embodiment, back surfaces 102 of the strip first and second sections 76 and 78 face each other in the folded extensible portion 72, and the elastic strip 82 is secured to the back surface 102 of the first and securement portions 68 and 70. The extensible portion 72 permits expansion of the tape strip 52 while the elastic strip 82 constrains longitudinal extension of the tape strip 52.

Another embodiment of the present invention is illustrated in FIGS. 13 and 14, in which like reference numerals designate like parts. In this embodiment, the diaper fastener has a pair of tape strips 52 and 52' on each of the diaper sides, with each of the tape strips 52 and 52' being similar to the fastener described in connection with FIGS. 1–4. As shown, the tape strip 52' is relatively narrow and the tape strip 52 is located intermediate the second tape strip 52' and the end edge 36 of the pad assembly 22. Also, the securement portions 70 and 70' of both tape strips 52 and 52' may be releasably attached to a common release sheet 54. In use, the securement portions 70 and 70' are peeled from the release sheet 54, and the larger tape strip 52 is utilized to secure the diaper about an infant, as shown in FIG. 14. Next, the second tape strip 52' may be attached to a lower spaced portion of the diaper in order to apply tension to this diaper portion after attachment, and secure a snug fit of the lower diaper portion about the infant.

Another embodiment of the present invention is illustrated in FIGS. 15–17, in which like reference numerals designate like parts. In this embodiment, the primary tape strip 52 has a first portion 68 attached to the back surface 26 of the pad assembly 22, and the securement portion 70 is releasably attached to a release sheet 54 on the front surface 30 of the pad assembly 22. As shown, the tape strip 52 has a cut-out 104 adjacent the side edge 34 of the pad assembly, and an auxiliary strip 106 extends through the cut-out 104. The auxiliary strip 104 has an adhesive-bearing securement portion 108 releasably attached to a back release surface 110 of the tape strip securement portion 70, and an elastic strip 112 extending between the securement portion 108 and the pad assembly where an end 114 of elastic strip 112 is secured to the diaper beneath the first strip portion 68. In use, the securement portion 70 of the tape strip 52 is utilized to secure the diaper about an infant, as shown in FIG. 17. Next, a tab 116 on the auxiliary strip 106 is utilized to peel the securement portion 108 from the tape strip 52, and the securement portion 108 of the auxiliary strip 106 is attached to a lower spaced portion of the diaper. Thus, the elastic strip 112 of the auxiliary strip 106 causes tension on the lower part of the diaper to obtain a snug fit of this diaper part about the infant.

The foregoing detailed description is given for clearness of understanding only, and no unnecessary limitations should be understood therefrom, as modifications will be obvious to those skilled in the art.

I claim:

1. A disposable diaper, comprising:
   an absorbent pad assembly having opposed surfaces, a pair of side edges, and a pair of end edges connecting the side edges; and
   a tape fastener comprising, tape means having a first portion secured to one of said surfaces of the pad assembly, a securement portion for attachment to a spaced portion of the diaper, an extensible portion connecting said first and securement portions, and elastic means constraining expansion of said extensible portion.

2. The diaper of claim 1 including release sheet means releasably attached to said securement portion.

3. The diaper of claim 2 wherein said first portion is located adjacent a side edge, and in which the release sheet means is attached to the other surface of said pad assembly.

4. The diaper of claim 2 wherein said release sheet means is attached to said one surface of the pad assembly.

5. The diaper of claim 4 wherein said first portion is spaced from said side edge, and said release sheet means is located adjacent said side edge.

6. The diaper of claim 4 wherein said tape means is generally aligned with an edge of the pad assembly.

7. The diaper of claim 6 wherein said tape means is located adjacent an end edge of the pad assembly.

8. The diaper of claim 4 wherein said release sheet means is located adjacent said first portion.

9. The diaper of claim 1 including a second tape means attached to the pad assembly and having a securement portion, an extensible central portion, and elastic means constraining expansion of the extensible portion.

10. The diaper of claim 9 wherein the first tape means is located intermediate the second tape means and an end edge of the pad assembly.

11. The diaper of claim 1 wherein said tape means includes a front adhesive bearing surface, said extensible portion comprises a fold in the tape means defining first and second sections folded with their front surfaces facing each other, and the elastic means extends across the extensible portion on the front surface of the tape means.

12. The diaper of claim 1 wherein said tape means includes a front adhesive bearing surface and an opposed back surface, said extensible portion comprises a fold in the tape means defining first and second sections folded with their back surfaces facing each other, and the elastic means extends across the extensible portion on the back surface of the tape means.

13. A disposable diaper, comprising:
   an absorbent pad assembly having opposed surfaces; and
   a tape fastener comprising, a pressure-sensitive tape strip having an adhesive bearing front surface, a first portion including at least a part thereof attached to one of said surfaces of the pad assembly, a securement portion remote the first portion, an extensible central portion having a fold defining a first section extending between the fold and said first portion and a second section extending between the fold and said securement portion, with the front surface of the first section facing the front surface of the second section, and an elastic strip extending across the extensible portion on the front surface of the tape strip, said elastic strip connected to said first portion and securement portion and constraining expansion of the extensible portion.

14. The diaper of claim 13 wherein the front surfaces of said first and second sections are free of adhesive.

15. The diaper of claim 13 wherein the front surfaces of the first and second sections include adhesive, and including sheet means covering the adhesive on the first and second sections.

16. The diaper of claim 13 wherein the elastic strip has opposed ends secured to the tape strip by adhesive on the first and securement portions.

17. The diaper of claim 13 wherein the elastic strip includes adhesive attached to said first and securement portions.

18. The diaper of claim 17 wherein adhesive on opposed ends of the elastic strip are attached to adhesive on the first and securement portions.

19. The diaper of claim 13 including a pair of relatively short anchoring strips having an adhesive bearing surface securing opposed ends of the elastic strip to said first and securement portions.

20. The diaper of claim 13 including an anchoring strip having a length greater than the length of the elastic strip, an adhesive bearing surface attaching to an outer surface of the elastic strip, opposed ends attached to said first and securement portions, and a slit separating opposed ends of the anchoring strip intermediate the opposed ends of the elastic strip.

21. The diaper of claim 13 wherein said first portion of the tape strip is spaced from a side edge of the pad assembly, and including a release sheet attached to said one surface of the pad assembly adjacent said side edge, with adhesive on said securement portion being releasably attached to an outer release surface of the release sheet.

22. The diaper of claim 13 wherein said first portion is attached to said one surface adjacent a side edge of the pad assembly, and including a release sheet attached to the other surface of the pad assembly adjacent said side edge, with adhesive on said securement portion being releasably attached to an outer release surface of the release sheet, and with said extensible portion being located adjacent said side edge.

* * * * *